United States Patent
Eberhart et al.

(10) Patent No.: US 7,803,124 B2
(45) Date of Patent: *Sep. 28, 2010

(54) GUIDEWIRE MOUNTED BALLOON MODULATION DEVICE AND METHODS OF USE

(75) Inventors: Mark Eberhart, Glenmoore, PA (US); William T. Fisher, Schwenksville, PA (US); John E. Nash, Chester Springs, PA (US); Dennis M Sauro, Glenmoore, PA (US)

(73) Assignee: Kensey Nash Corporation, Exton, PA (US)

( * ) Notice: Subject to any disclaimer, the term of this patent is extended or adjusted under 35 U.S.C. 154(b) by 922 days.

This patent is subject to a terminal disclaimer.

(21) Appl. No.: 10/928,027

(22) Filed: Aug. 28, 2004

(65) Prior Publication Data

US 2005/0080357 A1     Apr. 14, 2005

Related U.S. Application Data

(63) Continuation-in-part of application No. 10/840,727, filed on May 6, 2004, which is a continuation-in-part of application No. 10/227,996, filed on Aug. 26, 2002, now Pat. No. 6,902,535.

(51) Int. Cl.
*A61B 5/00* (2006.01)
(52) U.S. Cl. ............... 600/585; 604/96.01; 604/99.01; 604/104; 606/191
(58) Field of Classification Search ........... 600/583, 600/573, 580–582, 585; 604/96; 606/181, 606/194

See application file for complete search history.

(56) References Cited

U.S. PATENT DOCUMENTS

| | | | |
|---|---|---|---|
| 3,477,438 A | 11/1969 | Allen et al. |
| 3,495,594 A | 2/1970 | Swanson |
| 3,837,381 A | 9/1974 | Arroyo |
| 4,332,254 A | 6/1982 | Lundquist |
| 4,653,539 A | 3/1987 | Bell |
| 4,654,027 A | 3/1987 | Dragan et al. |
| 4,752,287 A | 6/1988 | Kurtz et al. |

(Continued)

FOREIGN PATENT DOCUMENTS

WO    WO-97/27896    8/1997

(Continued)

*Primary Examiner*—Max Hindenburg
*Assistant Examiner*—Fangemonique Smith
(74) *Attorney, Agent, or Firm*—Jeffrey R. Ramberg (57) ABSTRACT

An apparatus for modulating the pressure of a fluid such as a gas within the expandable portion of a guide wire catheter. A preferred embodiment apparatus features a mechanism for controllably gripping and releasing the open, proximal end of a tubular guide wire, a mechanism for introducing a fluid to a desired pressure and volume into the expandable portion of the tubular guide wire through the open end, and, while maintaining the pressure and volume of fluid in the tubular guide wire, a mechanism for introducing a sealing member into the chamfered, open end of the tubular guide wire to consistently seal the fluid in the tubular guide wire. In a particularly preferred embodiment, the apparatus also features a deflation tool for piercing the seal and letting the fluid out. Using this apparatus, the tubular guide wire can be re-sealed and re-opened as necessary.

24 Claims, 5 Drawing Sheets

U.S. PATENT DOCUMENTS

| | | | |
|---|---|---|---|
| 4,759,751 | A | 7/1988 | Gabel et al. |
| 4,790,813 | A | 12/1988 | Kensey |
| 4,911,163 | A | 3/1990 | Fina |
| 5,024,668 | A * | 6/1991 | Peters et al. ............... 606/194 |
| 5,749,371 | A | 5/1998 | Zadini et al. |
| 5,807,330 | A | 9/1998 | Teitelbaum |
| 6,017,323 | A * | 1/2000 | Chee ....................... 604/96.01 |
| 6,176,844 | B1 | 1/2001 | Lee |
| 6,179,815 | B1 | 1/2001 | Foote |
| 6,234,996 | B1 | 5/2001 | Bagaoisan et al. |
| 6,251,084 | B1 * | 6/2001 | Coelho ....................... 600/585 |
| 6,325,778 | B1 | 12/2001 | Zadno-Azizi et al. |
| 6,348,048 | B1 | 2/2002 | Andrea et al. |
| 6,431,039 | B1 | 8/2002 | Jacobsen et al. |
| 6,475,185 | B1 | 11/2002 | Rauker et al. |
| 6,622,731 | B2 * | 9/2003 | Daniel et al. ................ 128/898 |
| 6,902,535 | B2 * | 6/2005 | Eberhart et al. ............. 600/585 |
| 2001/0016704 | A1 | 8/2001 | Zadno-Azizi et al. |
| 2003/0088194 | A1 * | 5/2003 | Bonnette et al. ............ 600/585 |
| 2003/0088262 | A1 | 5/2003 | Bonnette et al. |
| 2003/0088263 | A1 | 5/2003 | Bonnette et al. |

FOREIGN PATENT DOCUMENTS

| | | |
|---|---|---|
| WO | WO-99/42161 | 8/1999 |

* cited by examiner

GUIDEWIRE MOUNTED BALLOON MODULATION DEVICE AND METHODS OF USE

RELATED APPLICATION

This application is a Continuation-In-Part of U.S. patent application Ser. No. 10/840,727 filed on May 6, 2004, entitled "Guidewire Mounted Balloon Modulation Device And Methods Of Use", which is a Continuation-In-Part of U.S. patent application Ser. No. 10/227,996, filed on Aug. 26, 2002, now U.S. Pat No. 6,902,535 both of which are assigned to the same assignee as this invention, and whose disclosures are incorporated by reference herein.

BACKGROUND OF THE INVENTION

The invention generally relates to interventional or surgical procedures, specifically relating to interventional cardiology and other intra-luminal procedures. The invention more particularly concerns a valve mechanism that allows modulation of pressure within a balloon or expandable member attached to, or otherwise located thereon, of a guidewire or other catheter-like instrument.

The use of a balloon attached to the end of a guidewire is not new, see for example U.S. Pat. No. 6,251,084 (Coelho), and U.S. Pat. No. 4,790,813 (Kensey). In this arrangement, the guidewire is actually a small diameter tube, with the lumen therethrough serving to allow fluid to be injected, and with the fluid being an agent used to expand the balloon.

The balloon may serve various functions (e.g., locating and/or securing the wire or associated device within the artery, securing a wire within a catheter, or blocking the distal flow of fluid and/or debris created during one or more of the procedures).

The balloon/guidewire system may be used in various types of therapeutic and/or diagnostic procedures (e.g., percutaneous transluminal angioplasty, stent placement, the placement of ultrasonic or other diagnostic instruments, and the placement of thrombectomy devices, etc.). During the procedure several catheters or elongate instruments (together "catheters") may be used sequentially, with the same guidewire. Inserting instruments over, or alongside, a single guidewire saves procedural time, since only one guidewire would need to be placed. This approach may also improve safety, and reduce chance of infection, etc.

Inserting a plurality of catheters, whether singularly or concurrently, requires the catheter(s) to be placed over the proximal end of the guidewire. Where the guidewire is arranged with a balloon at or near the distal end, the catheter(s) would need to be passed over any valve located at the proximal end of the guidewire.

Multiple catheters are commonly used when, for example, a physician performs an angiogram or other diagnostic procedure, and then decides to perform angioplasty or other therapeutic procedure or other interventional procedure. Most interventional procedures will require the placement of a guidewire for the subsequent delivery of the interventional instruments, and more recently some guidewires incorporate distal balloons to protect the distal tissues from debris generated during those same procedures. Since treatment and diagnostic procedures are becoming more commonplace, and the advancements in each of these technologies have led to procedures using even more catheters. These catheters are continually getting smaller, which allows the physician to reach tighter arteries and lumens within the body.

For distal protection to be effective the balloon must remain inflated as catheters are exchanged over the guidewire. This necessitates a small diameter valve, which some refer to as a low-profile valve. Self-sealing valves have previously been disclosed; see for example U.S. Pat. No. 3,477,438 (Allen, et al.), U.S. Pat. No. 3,495,594 (Swanson), U.S. Pat. No. 3,837,381 (Arroyo), and U.S. Pat. No. 4,752,287 (Kurtz, et al.). These valves are commonly made from elastic (Allen, et al., and Kurtz, et al.) or resilient (Swanson) materials, and may require pressure in the system to operate (Arroyo). The properties of these valve materials, together with their operational pressures, require various of these valves to have large sealing areas. This does not facilitate the design of smaller catheters. Additionally, the valves would ideally operate over a wide range of pressures; including positive and negative pressures.

Check valves have also been disclosed, see for example U.S. Pat. No. 4,653,539 (Bell), however these are directional valves, and therefore will not operate in both positive and negative pressure environments. Employing a vacuum in the system during navigation will facilitate the securing of the balloon to the guidewire, that is, the balloon will stay folded or otherwise securely pressed against the side of the wire. This may allow the system to navigate tighter vessels or lumens. However, check valves, such as the one disclosed by Bell, do not meet this bi-directional operation need. Additionally, this type of valve, as well as the previously described self-sealing valves, require a syringe or special instrument to allow evacuation around the valve's sealing surface. These syringes or needles must be in-place during the entire evacuation procedure, or the valve will cease the fluid flow. This opens the systems up to situations where malfunctions or equipment breakage may yield an inserted and expanded balloon, which may not readily be collapsed. A system is needed that will allow evacuation without the application of vacuum or other specialized components.

In addition to these stated concerns, the length of time required to complete the procedure is affected by these valves. This procedure time is of concern because of escalating medical costs, as well as the stress on the patient. These valves must allow rapid infusion and evacuation of balloon-filling fluids.

Yet another low profile catheter valve, designed to fit small diameter catheters to navigate small pathways within the body such as blood vessels and ducts, is disclosed in U.S. Pat. No. 4,911,163 (Fina). A syringe is attached to the proximal end of an elongated tubular conduit (e.g. catheter) and used to inflate a distal balloon. Once the balloon is inflated, the catheter is clamped at the proximal end, the syringe is removed, and a plug is inserted into the lumen of the catheter, and then the clamp is removed. The plug is retracted and reinserted to adjust the balloon inflation volume as needed, using this same multi-step procedure. Needless to say, this type of valve is tedious to handle and the need for a separate clamping system further complicates the procedure and may potentially damage the catheter. Certainly the clamping pressures are very high, in order to totally collapse the circular catheter bore such that fluid will not leak (until the plug is inserted). Reinflating the balloon would also cause integrity problems if the catheter were reclamped at the same location.

Another such low profile catheter valve is disclosed in U.S. Pat. No. 6,325,778 (Zadno-Azizi, et al.). This valve features a needle which is inserted coaxially with the guidewire, wherein the needle is arranged to cover a fluid outlet port. The rate of balloon inflation and collapse is limited by the rate at which gas leaves the fluid outlet port. Since the fluid outlet port is radially outward from the guidewire's longitudinal axis, its size is geometrically constrained; that is, the larger diameter of the port, the less strength the guidewire has. Since the guidewire must withstand significant bending and torsional stress during the procedure, the port must be significantly less than the inside diameter of the guidewire, thereby limiting the rate of evacuation of the balloon-filling fluid.

This slow evacuation phenomenon may have been recognized by Coelho, as the disclosure prescribes a vacuum to collapse the balloon. Indeed, the tortuous path in the orifice of the Coelho device, through which the balloon inflation fluid is evacuated, must be nearly as small as the one disclosed by Zadno-Azizi. Here, the orifice must be considerably smaller than the inside diameter of the guidewire, because the path of fluid escape is through a self-sealing valve; and the valve must have sufficient integrity to cause a seal against itself, after an evacuation needle is withdrawn.

A valve which may utilize the overall inside diameter (or bore) of the guidewire is disclosed in U.S. Pat. No. 5,807,330 (Teitelbaum). The two basic concepts disclosed by Teitelbaum are a valve that is basically an insert with threads, wherein the threads secure the valve in the proximal end of the guidewire; and an insert with a press-fit geometry, that is pressed into the proximal end of the guidewire. Both of these concepts suffer similar shortcomings.

The threaded insert requires extremely fine threads, which are expensive and tedious to manufacture even before considering the limited wall thickness of the guidewire available for threading (perhaps only a few thousandths of an inch). Additionally, it is extremely difficult to align small threaded parts of this sort, which leads to misalignment and cross-threading. This problem would be especially prevalent where the same valve was actuated more than once during the same procedure—a common occurrence.

The press-fit geometry requires parts of very tight tolerance, which are also tedious and expensive to produce. Press-fit components are normally manufactured for mechanical support, but press-fitting to cause a gas impermeable seal is possible; however, the insert would require an extremely uniform surface, which mates exactly with the inside surface at the proximal end of the guidewire. It is this guidewire surface which poses great manufacturing challenges.

Boring or machining the inside surface of the guidewire is very challenging because of the fine wall thickness—perhaps only a few thousandths of an inch. Machining of this component may produce irregular wall thinning, since no tube inside and outside is truly concentric, which could lead to premature failure.

The aforementioned threaded and press-fit concepts disclosed by Teitelbaum both suffer manufacturing challenges as well as economic disadvantages. Finally, they have features that may lead to premature failure, necessitating removal of the device, following by re-insertion of a new balloon/guidewire assembly.

It is the intent of the embodiments of the present invention to overcome these and other shortcomings of the prior art.

SUMMARY OF THE INVENTION

These and other objects of this invention are achieved by providing a valve mechanism for inflating and deflating a balloon or other expandable member on a guidewire or catheter (e.g., at or near the distal end of a guidewire), such that while the balloon is inflated, the proximal end of the wire would have a low profile and would not interfere with the use of other interventional devices using over-the-wire technique or rapid exchange systems. The system basically consists of detachable tools, one each for inflation and deflation of the balloon; additionally the inflation tool features in a preferred embodiment a gripping device, an inflating device, and a sealing device.

The inflation tool serves the functions of gripping and releasing the guidewire proximal end; providing a structure for modulating the pressure inside the guidewire resulting in balloon or expandable member inflation; and applying a deformable plug into the bore of the guidewire.

In use, the proximal end of the guidewire is inserted into a chamber of the inflation tool; pressure is introduced via the inflation device thereby inflating the balloon or expandable member. The detachable inflation tool inserts a malleable plug in the proximal bore of the guidewire, thereby avoiding the need for costly machining and stringently tight tolerances of other devices, in order to maintain pressure within the guidewire upon the detaching the inflation tool. The sealing device prevents the escape of fluid (e.g., gas or liquid) from the guidewire for the duration of the procedure, or until release of pressure becomes necessary. In a preferred embodiment, the guidewire is preconditioned, for example, to prevent or remove obstacles to proper sealing, e.g., distortions, debris or protrusions. Particularly preferred is to chamfer the open proximal end of the guidewire.

The deflation tool serves the function of relieving the pressure in the balloon or expandable member of the guidewire, by piercing the sealing device in the proximal bore of the guidewire, and upon tool removal allows the fluid contained therein to escape. The valve mechanism herein described allows repeated inflation and deflation of the catheter or guidewire, by engaging the appropriate inflation or deflation tool.

DETAILED DESCRIPTION OF PREFERRED EMBODIMENTS

Description of Inflation Tool

Figure 1:
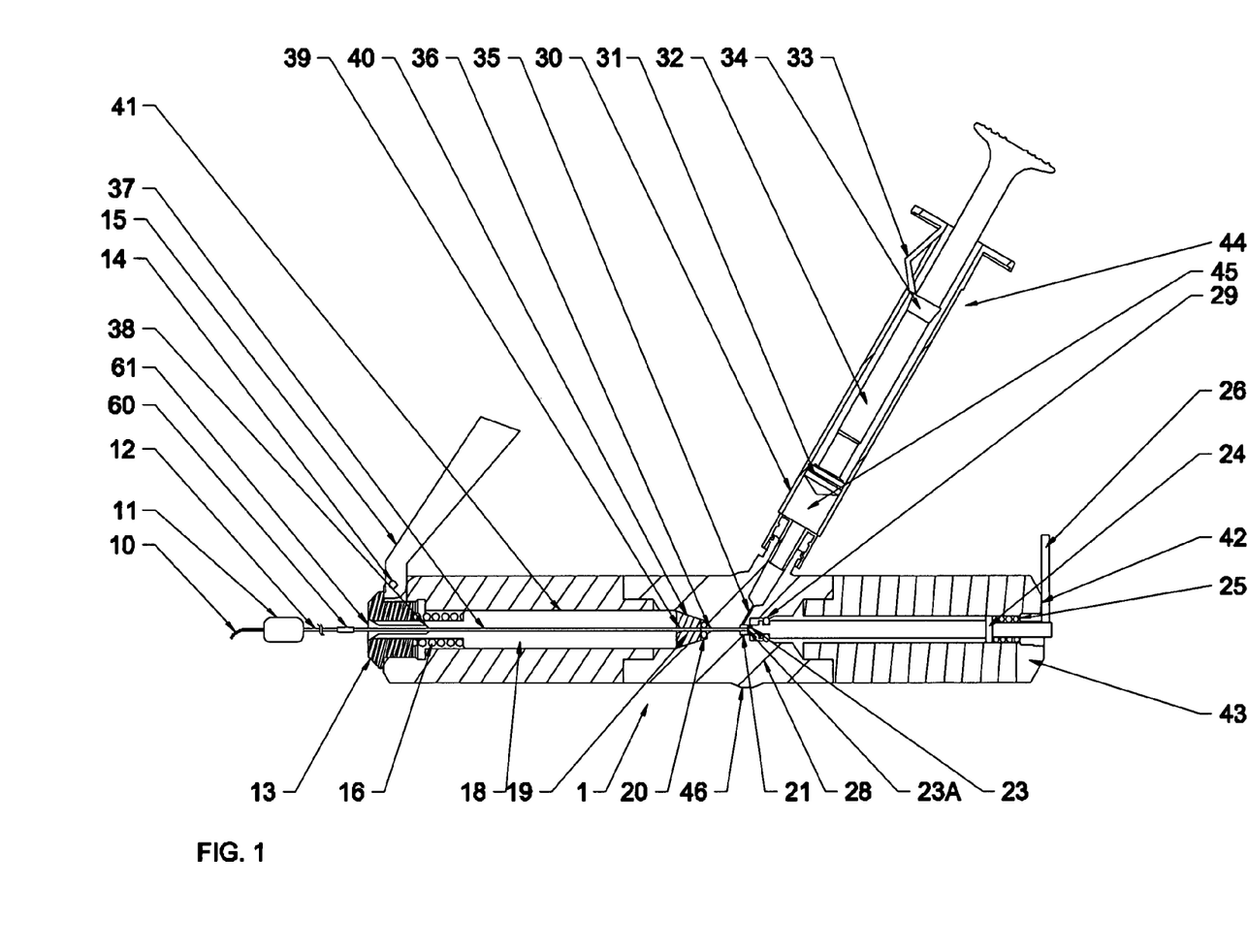
FIG. 1 is a sectional view of one design of tool for applying the sealing plug.
Figure 2:
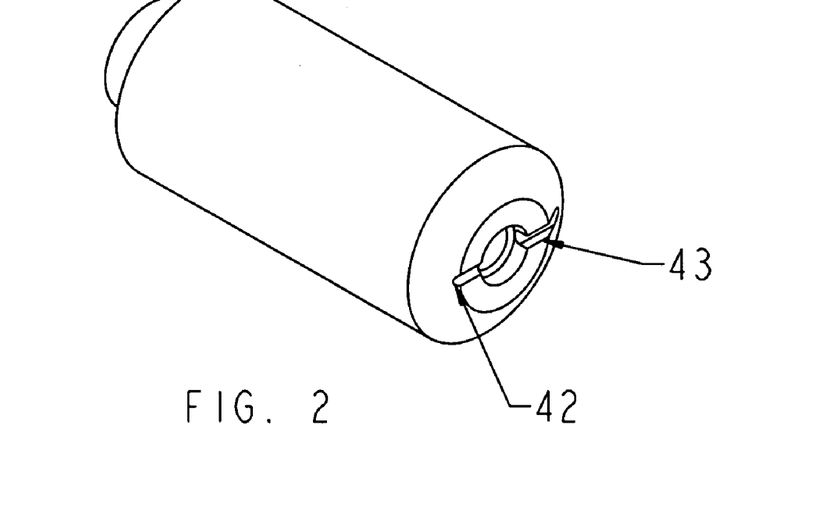
FIG. 2 is a perspective view of the sealing plug holding rod.
Figure 3:
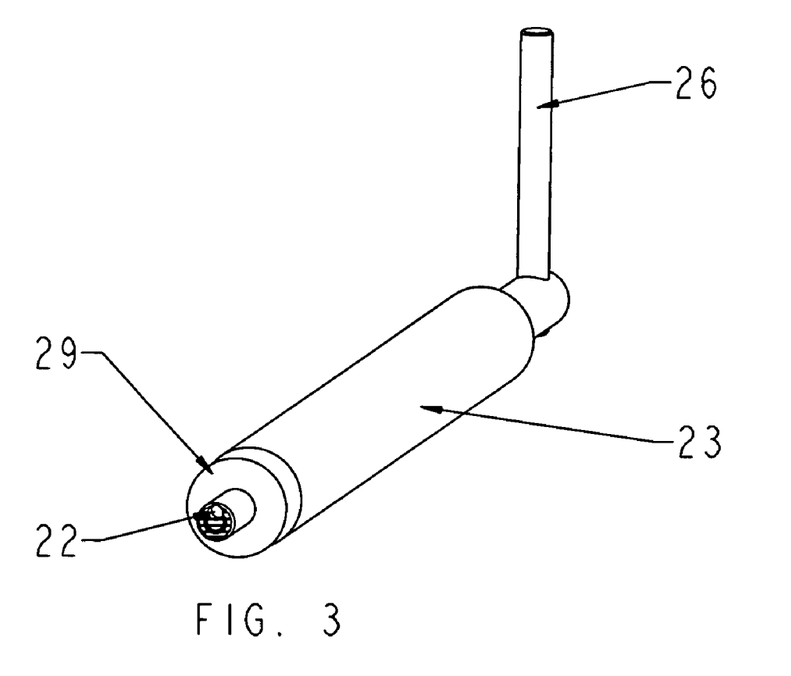
FIG. 3 is a perspective view of the cam sleeve.

The preferred embodiment tool shown in FIGS. 1, 2 and 3, performs various functions, including but not limited to:
a) Gripping and releasing the guidewire proximal end;
b) Inflating the balloon on the distal end of the guidewire, or placed somewhere therealong; and
c) Applying a sealing member in the proximal bore of the guidewire.

These various device embodiments comprise a sealing device, a gripping device, and an inflation device; while a separate device performs deflation. It is recognized that the device arranged for deflation may be attached to the device arranged for inflation (for convenience), although they may not share any componentry other than structural or housing. Additionally, it is contemplated by this invention that an inflation device or "inflation tool" may not necessarily comprise each of gripping, an inflation, and sealing structures. As a non-limiting example, it is recognized that the inflation device may be a traditional syringe (where the inflation device was arranged to accept same). It is also recognized that the gripping device may be useful to perform other functions (e.g., gripping tubes at diagnostic and/or therapeutic equipment inlet ports, e.g., those found on bypass and dialysis machines.)

Referring now to FIGS. 1, 2, and 3, describing a preferred embodiment of the inflation tool, wherein like numbers indicate like components. A preferred gripping device is disclosed, wherein a tubular guidewire 12, enters bore 37 in shaft 18 and passes through deformable member 19, through pierceable diaphragm 20, into cavity 21, and stops against the face 23A of rod 23. Shaft 18 is slidably mounted in bore 41 of housing 28, and, driven proximally (relative to the guidewire 12) by spring 16, thereby compressing deformable member 19 against the tapered bore 40 in housing 28. Pierceable diaphragm 20 is an intact disc until pierced by the entering tubular guidewire 12, the purpose of the diaphragm being to capture a charge of fluid (e.g., $CO_2$ or saline) in cavities 45, 21, and channel 35, prior to the piercing by the guidewire 12. Axial compression of the deformable member 19 results in the tubular guidewire 12 being gripped as the deformable member is moved radially inward by the taper 40.

In a preferred embodiment, the deformable member 19 may serve to create an impermeable seal around the outside diameter of the guidewire while gripping the guidewire. The impermeable seal may be effected through the application of a compressing action applied to the deformable member. This peripheral impermeable seal may beneficially serve to prevent the charge of fluid, once released, from escaping along the outside of the guidewire, and avoids or minimizes the possibility of an incomplete delivery of fluid into the guidewire (as will be discussed). An alternative to the pierceable diaphragm for retaining the charge of fluid in the cavity 21 and 45 is to ship the assembly with a smooth mandrel gripped in the deformable member 19 (not shown).

In a preferred embodiment, the gripping device further features an insertion-release structure, wherein the shaft 18 can be driven distally (relative to the guidewire 12) by movement of lever 15 which, pivoting on pin 14, moves the cone 17 attached to shaft 18. Thus movement of the lever 15 radially inward relieves the pressure on the deformable member 19 and hence releases the guidewire 12 (the same feature may also be used in reverse, to assist the entry of the guidewire into the device, as will be described later).

In a preferred embodiment the inflation tool features a sealing device, with the sealing device arranged to deliver a sealing member material into the guidewire to effect a seal, as will be described later. In this embodiment, the sealing device is preferentially located at the proximal end of the apparatus, wherein there exists a mounted rod 23 which can move axially and rotationally in bore 21A of housing 28. Rod 23 is driven distally by spring 25 acting through flange 24 and is restrained by arm 26 coming in contact with one of the grooves 42 or 43. An O-ring seal 29 seals rod 23 against bore 21A. A sealing member material 22 is inserted in an off center bore in rod 23. Surface 23A of rod 23 is striated with grooves 27 to permit flow of fluid into the bore of tubular guidewire 12.

In a preferred embodiment, the sealing member material is made from a plastically deformable or inelastic material, wherein such material may comprise organic and/or inorganic material. It is recognized that various materials may be suitable for this application, and the totality of material properties (e.g., strength, ductility, thixotropy, toughness, malleability, hysteresis, adhesiveness and fluid permeability, etc.) may reveal several good candidates.

In a preferred embodiment, the sealing material is a wax or other material that remains self-supporting at elevated temperatures, such as may be encountered during storage, shipment, and sterilization of the device. A self-supporting material obviates the need for a membrane or cover to maintain the material in place during the lifetime of the tool. As a benefit of not requiring a membrane or cover, there is less opportunity for debris or obstacles to interfere with a proper seal upon placement of the sealing material against the guidewire (as will be discussed later). A preferred embodiment of the sealing material will not flowably deform at the expected temperatures the device might be exposed to, as described above, and also remains able to maintain its shape against the pressure imparted by an inflated balloon or expandable member during a procedure. Furthermore, the sealing material remains plastically deformable at or around room temperature, so that it may easily be deformed, smeared or elongated, such as through the manual application of a deflation tool (as will be discussed later). Examples of materials suitable for use as a sealing material in the practice of the present invention include, but are not limited to: beeswax, paraffin wax, Tacky Wax (available from Bard's Products Inc), sculpting wax, modeling or plasticine clay, Tap-Ease (available from AGS Co.), and dental wax, such as Utility Wax, Neowax, Truwax-extra hard (all available from Denstply), and Modern Materials Shur wax (available from Heraeus Kulzer).

In a preferred embodiment the inflation tool features an inflation device. At the lower portion of FIG. 1 is shown a preferred embodiment of the inflation device, comprising an inflation syringe 44, wherein the syringe contains a barrel 30 arranged to be attached to body 28 using adhesive or a threaded joint (not shown). The charge of fluid is pre-charged into cavities 45, 21 and 35. A piston 31 attached to a plunger 32 drives fluid (gas or liquid) from chamber 45 via channel 35 into chamber 21 and thence into tubular guidewire 12. Another preferred embodiment additionally features a latch 33 fastened to barrel 30, wherein the latch 33 engages flange 34 after the plunger has been moved inward to deliver the fluid. The latch serves to prevent the piston and plunger from being driven back by the pressure trapped in cavity 21 (etc.) and balloon 11.

Figure 7:
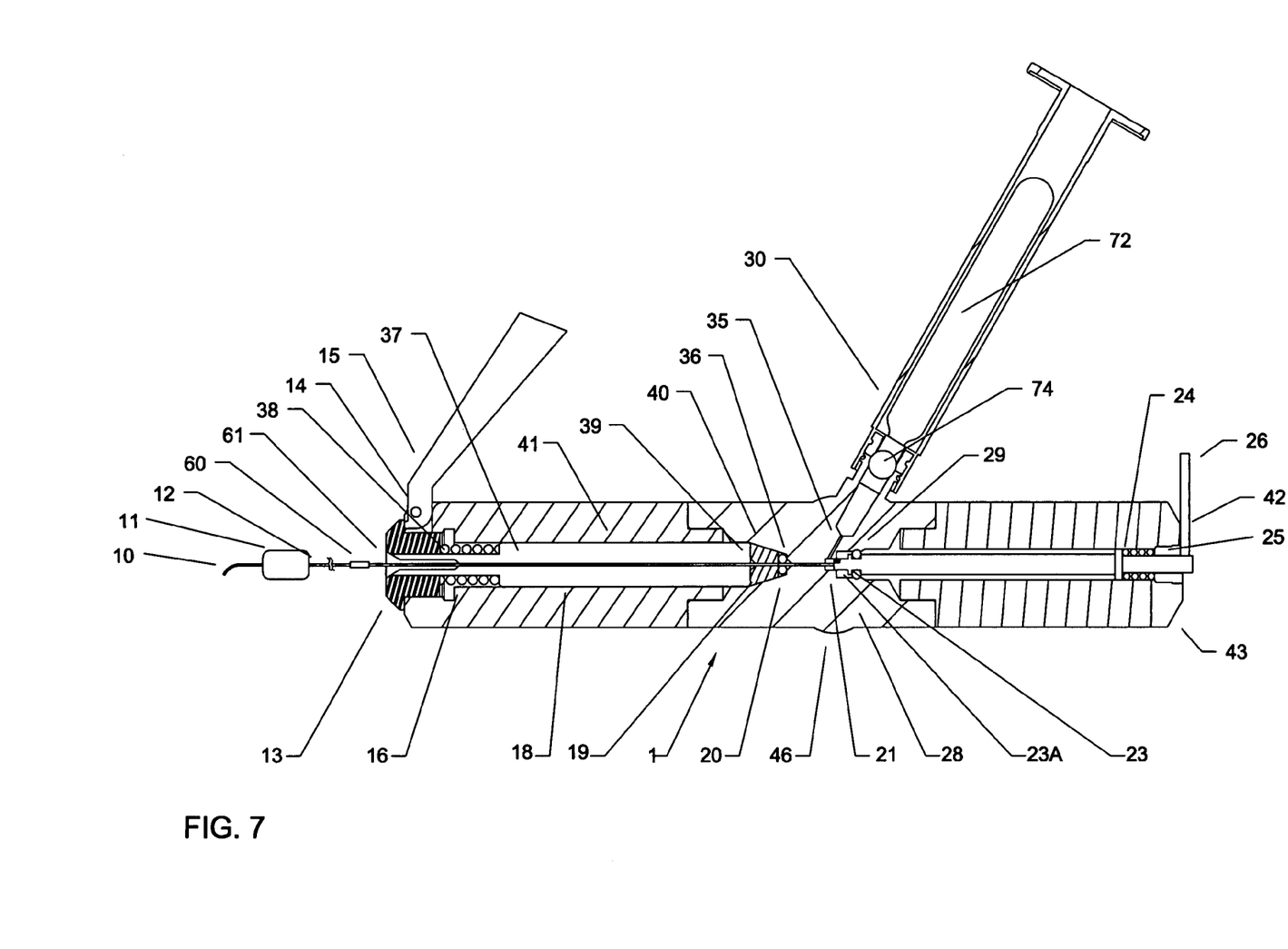
FIG. 7 is a sectional view of one design of tool for applying the sealing plug, where the inflation device utilizes a cylinder of a pressurized fluid.

In another preferred embodiment, as depicted in FIG. 7, the charge of fluid may be stored within a fluid reservoir, such as a cartridge or compressed gas cylinder 72 associated with the inflation tool 1. In this embodiment, the delivery of fluid from the fluid reservoir may be controlled with a regulator 74, or other technology known in the art, in order to deliver a precise pressure and/or flow rate of fluid. Preferably, the regulator would be easily adjustable, such that by simply adjusting the regulator, the extent of expansion of the balloon can be manipulated. The fluid charge may be delivered through the activation of a mechanism for releasing the charge, such as, for example, the penetration of a membrane upon the insertion of the guidewire end, or more preferably, through a controllable valve mechanism which controls fluid flow from the inflation device, either in the form of, or distinct from the regulator 74.

The charge of fluid contained within the fluid reservoir 72 is preferably large enough to support multiple balloon 11 inflations and inflation volume adjustments. In this manner, it becomes possible for a single inflation tool 1 to inflate, or adjust the volume in, a balloon repeatedly. In addition, the fluid reservoir may be renewable, such as a compressed fluid cartridge that may be separable from the inflation tool, whereupon after initial inflation(s), the spent cartridge 72 may be removed from the inflation device, and a second charged cartridge put in place, so that further inflation(s) of the balloon is possible.

Other methods are available for providing a reservoir of fluid for the balloon, (including the use of syringes as described above with reference to FIG. 1), which may preferably be separable from the inflation device using techniques known in the art (e.g., luer locks, threaded fittings, compression fittings, etc.). Ideally, these reservoir devices would allow operator control over the amount of volume and rate of fluid delivered to the balloon. Furthermore, through the incorporation of a checkvalve or other feature to prevent escape of fluid, the balloon after inflation by a syringe, compressed gas cartridge or other inflation methods, could be maintained in an inflated state, while the discharged unit is removed and replaced with a second inflation unit in order to deliver more volume to the balloon.

Description of Inflation Tool Use

A preferred embodiment inflation tool includes the gripping, inflation, and sealing devices in combination, and allows the operator to hold the assembly 1 in one hand and with the thumb and fore-finger to squeeze the lever 15 toward the body 28 thus moving shaft 18 distally and relieving pressure on the deformable member 19. The guidewire 12 is then inserted into shaft 18, centralized by the tapered inlet 38, passed through the deformable member 19, to pierce the diaphragm 20 and come to rest against rod 23 at surface 23A. Chamfers at 39 and 36 further aid in centralizing the guidewire. Surface 23A of rod 23 is striated with fine grooves 27 to permit flow of fluid into the bore of tubular guidewire 12. In an alternate embodiment, the guidewire may be formed such that when placed against rod 23 whose surface 23A is smooth (not shown), at least one fluid channel remains available for the passage of fluid therethrough. This may be accomplished by creating an angle cut in the guidewire end, such that when urged against the surface 23A, only a portion of the circumference of the guidewire is contacting the surface. Alternatively, an undulating, wavy, castellated or uneven cut may be employed, where alternating sections of the circumference of the guidewire will contact the surface 23A. In any event, in this embodiment there should be some fluid channel remaining for the passage of fluid once the guidewire is placed against the surface of the rod.

In these preferred embodiments, for example, when the guidewire has bottomed on surface 23A, the user releases the lever 15, whereupon the shaft 18 is propelled to proximally and deformable member 19 is placed in compression. In turn this action, through taper 40 or squeezing action, causes the deformable member 19 to grip the guidewire 12 securely, and may enhance the impermeable peripheral seal created at the interface of the guidewire and the deformable member, as previously discussed.

In a preferred embodiment, the position of the guidewire may be confirmed visually by viewing the location via the lens 46 built in to a clear plastic housing 28. Alternatively, if the housing is made from an opaque material the viewing lens 46 can be inserted in a tunnel as a separate component (not shown).

In yet another embodiment, the correct position of the guidewire 12 can alternatively be ascertained by observing the location of a contrasting band of color 60, formed on the guidewire 12, relative to the entrance 61 of shaft 18.

In the practice of the present invention, it may be preferred to provide a guidewire that has been preconditioned for use with the inflation tool and/or deflation tool. The preconditioning may involve a step taken to prevent the occurrence of obstacles to obtaining a proper seal. For example, during the manufacture of a guidewire, it is not uncommon for an imperfection or obstacle to obtaining a seal (e.g., distortion, debris, or protrusion) that remains within the bore of the guidewire 12. The removal of such an obstacle is preferred, such as by cleaning, grinding, or de-burring of the guidewire and bore to create a smooth clean surface for presentation of the sealing material. If steps are not taken to prevent the existence of an obstacle to sealing within the bore of the guidewire, the application of the sealing material may conform to that obstacle, and may not generate a proper seal with the wall of the bore.

Figure 6A:
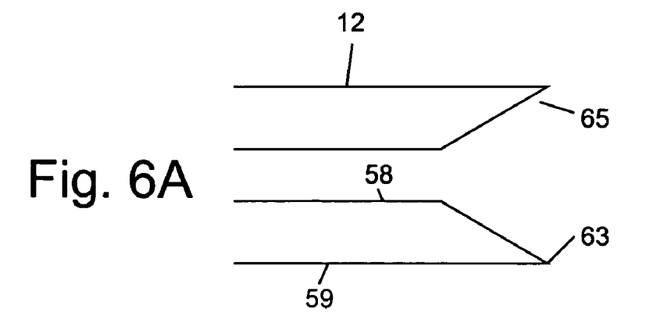
FIGS. 6A, B, C, and D are sectional views of various embodiments of the proximal end of a guidewire.
Figure 6B:
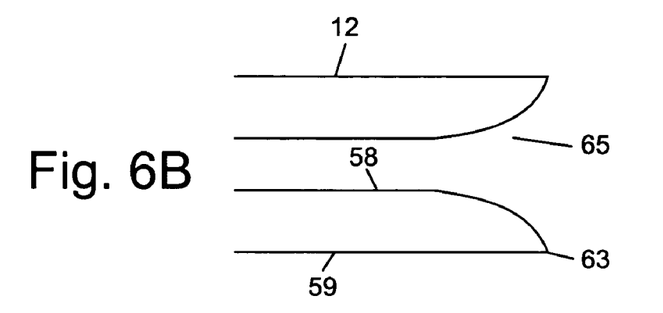
Figure 6C:
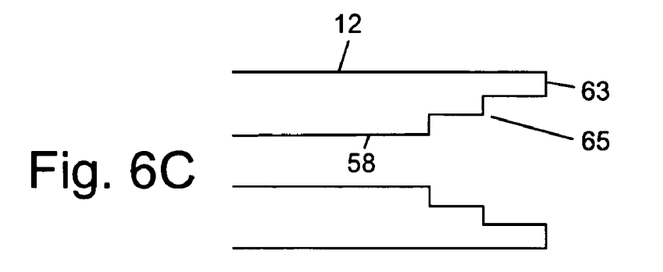

A preferred preconditioning step, useful for the practice of the current invention using a deformable sealing material, is to prepare the guidewire for achieving a consistent seal through the incorporation of a chamfer or bevel 65 at the entrance to the bore of the guidewire as can be seen in FIGS. 6A, 6B and 6C. In these embodiments, the chamfer would then allow the guide wire 12 to consistently accept the introduction of a sealing member when forming a seal. The chamfered end 65 of the guidewire 12 presents a leading edge 63 for receiving the sealing material, wherein the leading edge is of a greater diameter or cross-section than that of the adjacent segment of the guidewire inner bore 58 in which the sealing material will flow. Through the incorporation of this chamfer, the sealing material, as first inserted, has a diameter determined by the leading edge 63 (preferably the same as the outside diameter 59 of the guidewire 12), and as the sealing material is driven further into the guidewire, the constriction due to the cross-section reduction forces the sealing material to flow and elongate, thereby completely, and consistently, filling the entirety of the cross-section of the guidewire inner bore 58, and forming a leakproof seal to maintain balloon inflation.

Figure 6D:
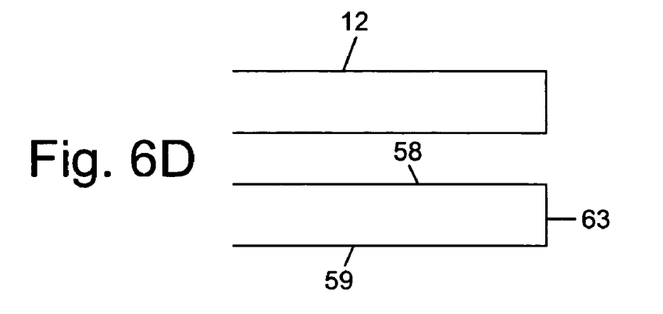

In contrast to a guidewire 12 where there is no chamfer, as shown in FIG. 6D, the leading edge 63 creates an opening similar in diameter and cross section to the sealing area of the guidewire inner bore 58, and the leading edge will shave off the excess sealing material creating a plug. However, in this embodiment, the deformable sealing material will not be forced to flow and elongate, as in the preceeding embodiment, as there is not a reduction in cross section, as the inner bore 58 is consistent over the length of the sealing area of the guidewire. Therefore, there may be a greater likelihood of an incomplete seal, as the sealing material may distort when inserted further into the guidewire, and lacks the consistently tight seal against the inner bore 58 of the guidewire 12 created by the elongation and flow of the sealing material, as described for FIGS. 6A, 6B and 6C.

Referring again to FIGS. 6A, 6B, and 6C, the chamfer 65 is preferably created through a chamfering process applied at the proximal end of the guidewire, though the chamfer may be created through other means. For example, an abrasive, cutting or polishing tool may be applied to the distal end of the guidewire, creating a taper thereon. In the case of FIG. 6A, a cutting tool, such as a tapered bit incorporating at least one cutting edge (i.e., an elongated triangle bit or pyramid bit) may be inserted into the end of the guidewire, and upon rotation, the cutting edge will remove a portion of the guidewire, thereby creating the chamfer 65 in the guidewire in the form of a beveled edge. Alternatively, the chamfer could be created as a radius curve (as seen in FIG. 6B) or stepped down decreases in diameter (as seen in FIG. 6C), where there is a chamfer or reduction in inner bore 58 diameter and cross section created at or near the open proximal end of the guidewire. It is recognized the chamfer could also be created by increasing the diameter of the leading edge of the guidewire, flaring out the proximal end, thereby creating an inner bore that features a reduction in cross-section, causing flow and elongation as the sealing material is applied. In this flared embodiment, care must be taken to ensure that the flaring of the proximal end does not increase the crossing profile to the point where a suitable catheter or wire would be unable to be smoothly applied over it.

Ideally, the chamfer 65 would feature a smooth reduction in diameter (as depicted in FIGS. 6A and 6B), creating the compression, flow and elongation of the deformable material upon insertion, as opposed to a consistent diameter inner bore (as shown in FIG. 6D), which would not cause the flowing of the deformable material to consistently fill the inner bore of the guidewire. Alternatively, a stepped reduction in inner bore diameter would have the effect of a chamfered edge (as depicted in FIG. 6C) and may result in the elongation and flow of the sealing material as a reduction in diameter is encountered, thereby causing the sealing material to flow under the compression to fill the inner bore and create an impermeable seal.

An additional sealing obstacle that may arise after a preconditioning step may be in the form of a membrane that is used to maintain the sealing material in place, such as when a flowable material is used as a sealing material. A protective membrane or cover, when being ruptured by the guidewire, may leave debris, such as membrane fragments, or otherwise interfere with the achievement of a fluid impermeable seal as the sealing material 22 placed into the guidewire. Utilizing a sealing material which is non-flowable over the encountered temperatures, as previously described, may thereby avoid the necessity for a membrane.

An additional or alternate preconditioning step may be employed to prepare the guidewire for application of a sealing material. There may be benefit to providing a coating or beneficial material within at least the proximal end portion of the bore of the guidewire 12, that facilitates entry or adhesion of sealing material in the bore of the guidewire. The beneficial material may be the same material as the sealing material 22, or may be a different suitable sealing material as described above, or alternatively a material such as adhesives, or tacky materials to encourage sealing material adhesion.

For example, an amount of the sealing material 22 may be inserted into or applied to the guidewire 12 before inflation (e.g., during manufacturing), and, before employment of the inflation tool. It is recognized the pre-placed sealing material may be shaped into a coating of the guidewire bore, such as is achieved through employment of the deflation tool or similar implement, or alternatively molten material may be painted or dipped into the interior bore.

Now returning to the preferred combination embodiment, the plunger 32 and attached piston 31 are then driven inward to propel the fluid in cavity 45 through channel 35 into cavity 21 and thence through the bore of guidewire 12 into the balloon 11. In the case where gas is used to inflate the balloon, the plunger 32 may be driven to the bottom of the bore and allowed to return to a position controlled by flange 34 and latch 33. This over-compression of the gas permits the initial pressure to be high to overcome the balloon resistance but drops the pressure as the balloon reaches full size, thus reducing the tendency to overpressure the vessel (not shown) in which the balloon is residing. The possibility for fluid escaping along the outside of the guidewire, rather than entering into the bore of the guidewire is minimized through the creation of the impermeable seal between the deformable member 19 and the guidewire 12. By ensuring that the charge of fluid is directed into the bore of the guidewire, rather than escaping, the full charge may be utilized to pressurize the balloon or expandable member of the guidewire. This impermeable seal increases the accuracy of the inflation of the balloon, and thus increases confidence that the balloon is correctly inflated. In particular, a fully inflated balloon usually is intended to completely occlude the lumen into which it is inserted.

Figure 4:
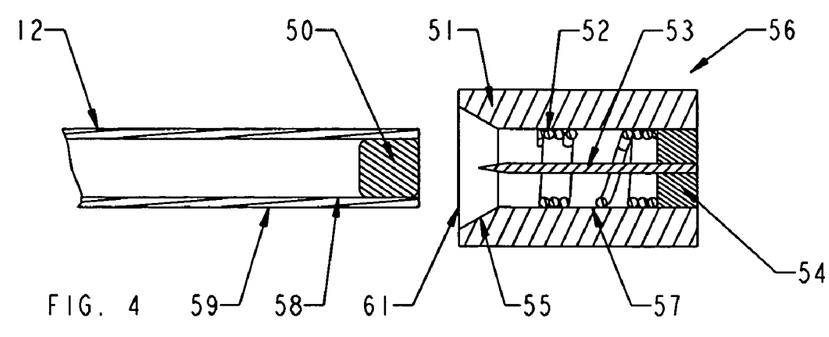
FIG. 4 is a sectional view of the deflation needle tool prior to application.

With the balloon 11 inflated in the vessel, the arm 26 is rotated 180 degrees in this example (but any other angle would work with slots 42 & 43 placed differently) so that rod 23 revolves to place the sealing material 22 to a position opposing the guidewire 12. Then spring 25 urges rod 23 distally and drives the sealing material 22 into the open end of tubular guidewire 10 thus trapping the fluid in the guidewire and balloon. A plug 50 of sealing material 22, is driven into the bore of the tubular guidewire 12, as shown in FIG. 4. It is recognized that the device may incorporate a plurality of locations having depots of sealing material incorporated in surface 23A of rod 23. In this manner, the arm 26 may repeatably be rotated a smaller fraction of a revolution, and place additional depots having sealing material 22 to a position opposing the guidewire 12. In this manner, the same device may be utilized to repeatedly seal the guidewire. This may be beneficial when multiple inflation and deflation steps are required for a procedure. Alternatively, in the event of a malfunction, or failed seal, another attempt could be made to maintain inflation without having to deflate the balloon.

In an embodiment of the device having the ability to repeatably inflate the balloon, or capable of incrementally increasing balloon inflation, there may be a benefit to coordinating the actions of the inflation and sealing mechanisms. For example, upon the act of causing balloon inflation, a suitable depot of sealing material may be moved into a ready position for sealing the guidewire. This may be accomplished, for example, through the use of a mechanical link mechanism, such as a drag-link mechanism or other mechanism known in the art, where the act of the operator in causing the inflation of the balloon, results in the rotation of the arm 26 by some amount in order to expose an additional depot of sealing material 22 for eventual insertion into the guidewire 12.

After sealing has been accomplished through the insertion of the sealing material into the guidewire, the lever 15 is again pressed inward radially and the guidewire is removed from the device, and the wire is ready for the rest of the interventional procedure, which might involve the passage of angioplasty balloons, stent balloons, diagnostic ultrasound, or other procedure requiring a balloon protected or anchored guidewire with the balloon inflated.

Description of Deflation Tool

Figure 5:
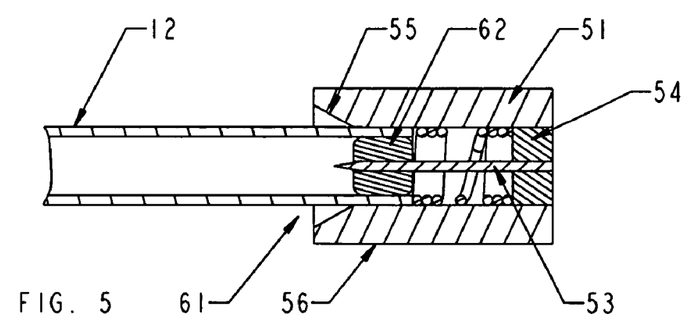
FIG. 5 is a sectional view of the deflation needle tool during application.

Referring to FIGS. 4 and 5, a preferred embodiment of the deflation tool 56 is basically constructed from four elements, a handle 51, a tube 54, a spring 52, and a needle 53. The handle has a bore 57 of about 0.016 inch diameter, a little larger than the outside diameter of the guidewire 12 which is typically 0.015 inch, and has a lead in taper 55 to allow the operator to easily locate the bore 57.

The proximal end (relative to the user's hand while utilizing the tool) of the needle 53 is held centrally in the bore 57 by tube 54. Tube 54, together with the needle 53, and the handle 51 can be assembled together by any convenient means, including but not limited to welding, using an adhesive, or a crimping operation. The needle is approximately 0.005 inch in diameter in this embodiment, and is supported by the spring coils 52 to prevent the needle from being bent during use and to align the distal end (relative to the user's hand while utilizing tool) of the needle on the centerline of the bore 57. The length of the plug 50 of sealing member material 22 (see FIG. 1) in the proximal end of the guidewire 12 is preferably about 0.030 inch long axially, although other dimensions may be more suitable depending on the composition of the sealing material and the pressure at which the balloon requires. The guidewire outside diameter 59 is typically 0.015 inch and the bore 58 can typically range from 0.011 inch to 0.005 inch. The needle needs to be sufficiently large to provide a bore through the plug 50 that it will allow the balloon to be deflated rapidly, but not so large that the plug 50 is smeared along the bore 58 too far to require a very long needle. It has been found that a 0.005 inch diameter needle permits deflation times that are acceptable (less than 30 seconds), utilizing a 0.007 inch diameter guidewire bore. Clearly these dimensions are examples only and could be adjusted to accommodate guidewires or catheters of different diameters.

The deflation tool embodiment described can be used multiple times, but it is unlikely that the operator will ever need to inflate and deflate the balloon more than 5 times in a procedure. The needle 53 is therefore preferably required to penetrate several times the length of the plug 50 into the guidewire bore 58 for this to be achieved.

Description of Deflation Tool Use

The operator inserts the proximal end of the guidewire 12 into the lead taper 55 of the deflation tool 56 compressing the spring 52 to the fully compressed condition. The plug 50 is pierced as shown in FIG. 5, and smears into an elongated tubular shape 62 concentric to the bore 57. The sealing material can be plastically deformed at or near room temperatures, and would easily be deformed and conform to an inserted needle or other manually operated device, which creates the elongated tubular shape. The hollow opening created in the elongated tubular shape of sealing material allows the fluid contained under pressure within the guidewire 12 to escape. The balloon 11 (see FIG. 1) then deflates due to its inherent elastic recovery, and/or vacuum can be applied to the tubular guidewire 12 by syringe or other means (neither shown) to accelerate the deflation time. The tool is then removed and is available for any subsequent use. A deflation tool as described obviates the need to remove the sealing material from the guidewire, either by removing the sealing material from the guidewire, or severing the sealed end, which could result in distortion of the tubular wire, and having the effect of variable deflation times and increased difficulty resealing.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. An apparatus for modulating the pressure of a fluid within an expandable portion of a catheter or guidewire, the apparatus comprising an inflation tool comprising:

means for controllably gripping an open proximal end of a catheter or guidewire, the gripping means comprising a deformable member and a deforming mechanism, the deforming mechanism arranged to act upon the deformable member to cause gripping of the catheter or guidewire, said deformable member being arranged to create an impermeable peripheral seal about an outside diameter of said catheter or guidewire upon actuation of said deforming mechanism;

means for introducing a fluid into said expandable portion of said catheter or guidewire through said open proximal end, thereby inflating said expandable portion of said catheter or guidewire to a desired extent; and means for sealing said open proximal end of said catheter or guidewire, wherein a bore of said open proximal end is chamfered, and wherein said sealing means is arranged to introduce a deformable sealing material into said open proximal end, and further wherein said deformable sealing material is arranged to conform to said chamfer and consistently seal said fluid in said catheter or guidewire.

2. The apparatus of claim 1, wherein said open proximal end is chamfered as a radius curve.

3. The apparatus of claim 1, wherein said open proximal end is chamfered as a beveled edge.

4. The apparatus of claim 1, wherein said open proximal end is chamfered in a stepped manner.

5. The apparatus of claim 1, wherein said means for introducing a fluid comprises a fluid reservoir.

6. The apparatus of claim 5, wherein said fluid reservoir is renewable.

7. The apparatus of claim 5, wherein said fluid reservoir comprises a cylinder of compressed gas.

8. The apparatus of claim 5, wherein said fluid reservoir comprises a syringe.

9. The apparatus of claim 5, wherein said means for introducing a fluid further comprises a regulator to control the flow and pressure of said fluid.

10. The apparatus of claim 5, wherein said fluid reservoir is arranged to inflate said expandable portion of said guidewire a plurality of times.

11. The apparatus of claim 1, wherein said means for introducing a fluid and said means for sealing are mechanically linked, whereupon actuating said means for introducing a fluid prepares the means for sealing for application.

12. The apparatus of claim 1, wherein said deformable sealing material is capable of maintaining an elevated pressure within said expandable portion of said catheter or guidewire.

13. The apparatus of claim 12, wherein said sealing material, while at or near room temperatures is able to resist shearing loads generated by elevated pressure within said expandable portion of said catheter or guidewire.

14. The apparatus of claim 12 wherein said sealing material is selected to be self-supporting during sterilization, shipment and storage.

15. The apparatus of claim 14, wherein said sealing material is plastically deformable at room temperature.

16. The apparatus of claim 12, wherein said means for sealing said open proximal end further comprises a rod comprising at least one flat surface, and being capable of axial and rotational movement, wherein said sealing material is housed in a plurality of bores arranged in said flat surface, said flat surface being arranged to contact said open end of said catheter or guidewire.

17. The apparatus of claim 16, wherein said rotational movement of said rod enables each of said bores to be rotated into alignment with said open proximal end, thereupon said sealing material may repeatably be inserted into said open proximal end.

18. The apparatus of claim 16, wherein said rod is positioned proximally to said catheter or guidewire and moved axially in a distal direction, towards said open proximal end, thereby inserting said sealing material into said open proximal end.

19. The apparatus of claim 1, wherein said open proximal end of said catheter or guidewire comprises a smooth, clean surface amenable to sealing.

20. The apparatus of claim 19, wherein said smooth, clean surface is free from obstacles to sealing said open proximal end of said catheter or guidewire.

21. The apparatus of claim 20, wherein said smooth, clean surface is free from burrs, protrusions, distortions and debris.

22. The apparatus of claim 1, wherein said open proximal end further comprises a coating on an interior bore of said open proximal end, said coating comprising a beneficial material to encourage effective sealing.

23. The apparatus of claim 22, wherein said beneficial material comprises a material that facilitates adhesion of said sealing material in said bore.

24. An apparatus for modulating the pressure of a fluid within an expandable portion of a catheter or guidewire, the apparatus comprising an inflation tool comprising:

means for controllably gripping an open proximal end of a catheter or guidewire, the gripping means comprising a deformable member and a deforming mechanism, the deforming mechanism arranged to act upon the deformable member to cause gripping of the catheter or guidewire;

means for introducing a fluid into said expandable portion of said catheter or guidewire through said open proximal end, thereby inflating said expandable portion of said catheter or guidewire to a desired extent; and means for sealing said open proximal end of said catheter or guidewire, wherein an entrance to a bore of said open proximal end is chamfered, whereby a leading edge of said bore has a greater cross-section than that of an adjacent segment of said bore, and wherein said sealing means is arranged to introduce a deformable sealing material into said open proximal end, and further wherein as said deformable sealing material is driven into said guidewire or catheter, a constriction due to a reduction of said cross-section forces said sealing material to flow, thereby completely filling the entirety of the cross-section of the adjacent segment of said bore.

\* \* \* \* \*